United States Patent
Ricou et al.

(12)

(10) Patent No.: US 10,363,549 B2
(45) Date of Patent: Jul. 30, 2019

(54) CHROMIUM OXYFLUORIDE CATALYSTS HAVING HIGH FLUORINATION ACTIVITY

(71) Applicant: Arkema Inc., King of Prussia, PA (US)

(72) Inventors: Pierre Ricou, Ardmore, PA (US); Nicolas Doucet, Cuvry (FR); Anne Marie Pigamo, Francheville (FR)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 15/748,246

(22) PCT Filed: Aug. 3, 2016

(86) PCT No.: PCT/US2016/045238
§ 371 (c)(1),
(2) Date: Jan. 29, 2018

(87) PCT Pub. No.: WO2017/023966
PCT Pub. Date: Feb. 9, 2017

(65) Prior Publication Data
US 2018/0214855 A1    Aug. 2, 2018

Related U.S. Application Data

(60) Provisional application No. 62/201,130, filed on Aug. 5, 2015.

(51) Int. Cl.
| *B01J 27/12* | (2006.01) |
| *C07C 17/20* | (2006.01) |
| *B01J 21/04* | (2006.01) |
| *B01J 27/132* | (2006.01) |
| *B01J 27/32* | (2006.01) |
| *C07C 21/18* | (2006.01) |

(52) U.S. Cl.
CPC .............. *B01J 27/12* (2013.01); *B01J 21/04* (2013.01); *B01J 27/132* (2013.01); *B01J 27/32* (2013.01); *C07C 17/206* (2013.01); *C07C 21/18* (2013.01)

(58) Field of Classification Search
CPC ... C01P 2002/74; C01P 2002/85; B01J 27/12; B01J 27/132
USPC .................................. 502/228; 570/136, 165
See application file for complete search history.

(56) References Cited

U.S. PATENT DOCUMENTS

| 3,455,840 | A | * | 7/1969 | Kato ...................... B01J 27/06 |
| | | | | 502/159 |
| 4,155,881 | A | * | 5/1979 | Sullivan ................. B01J 27/12 |
| | | | | 502/228 |
| 6,150,572 | A | | 11/2000 | Rinaldi et al. |
| 9,193,809 | B2 | | 11/2015 | Kuzuba et al. |
| 10,227,275 | B2 | * | 3/2019 | Pigamo ................. C07C 17/206 |
| 2009/0240090 | A1 | | 9/2009 | Merkel et al. |
| 2011/0224466 | A1 | * | 9/2011 | Sharratt ................. B01J 23/26 |
| | | | | 570/165 |
| 2012/0116131 | A1 | * | 5/2012 | Sharratt ................. B01J 23/26 |
| | | | | 570/168 |

FOREIGN PATENT DOCUMENTS

EP      0 657 408 A1    6/1995

OTHER PUBLICATIONS

Seoyeon Lim et al., "Catalytic dehydrofluorination of 1,1,1,2,3-pentafluoropropane (HFC-245eb) to 2,3,3,3-tetrafluoropropene (HFO-1234yf) using in-situ fluorinated chromium oxyfluoride catalyst." Catalysis Today 293-294, pp. 42-48. (Year: 2017).*
A Comparative Study of Bulk and Supported Chromia Catalysts for the Flourination of Trichloroethylene—Rao, J. M. et al—Journal of Catalysis 184, 105-111 (1999).
Steag's Long-Term Catalyst Operatiing Experieince and Cost—Sobolewski, Han et al—Proceedings of the 2006 Environmental Controls Conference.
Flourination of CF3CH2Cl Over Cr—Mg Fluoride Catalyst—The Effect of Temperature on the Catalyst Deactivation—Hyunjoo Lee et al Journal of Catalysis 169, 307-316 (1997).

* cited by examiner

*Primary Examiner* — Patricia L. Hailey
(74) *Attorney, Agent, or Firm* — Steven D. Boyd

(57) ABSTRACT

X-Ray photoelectron spectroscopy (XPS) is used to assess or predict the catalytic activity of a chromium oxyfluoride catalyst in a reaction wherein a chlorinated compound is converted to a fluorinated compound.

17 Claims, No Drawings

CHROMIUM OXYFLUORIDE CATALYSTS HAVING HIGH FLUORINATION ACTIVITY

This present application is the national phase under 35 USC § 371 of prior PCT International Application Number PCT/US2016/045238 filed Aug. 3, 2016 which designated the United States of America and claimed priority to U.S. Provisional Patent Application Ser. No. 62/201,130 filed Aug. 5, 2015.

FIELD OF THE INVENTION

The present invention relates to chromium oxyfluoride catalysts which catalyze the fluorination of chlorinated compounds.

DISCUSSION OF THE RELATED ART

Methods for fluorinating chlorinated compounds using various types of catalysts are known in the art. For example, methods for reacting 1,1,2,3-tetrachloropropene with HF to produce 2-chloro-3,3,3-trifluoropropene (HFO-1233xf) and for reacting 2-chloro-3,3,3-trifluoropropene (HFO-1233xf) with HF to produce 2,3,3,3-tetrafluoropropene (HFO-1234yf), which is a promising substitute for hydrofluorocarbons with high global warming potential such as 1,1,1,2-tetrafluoroethane, have been developed. Chromium oxyfluoride catalysts have been of particular interest for such fluorination reactions. These catalysts comprise chromium, oxygen and fluoride and optionally additional components such as transition metals (e.g., nickel) as co-catalysts. Their general empirical formula is commonly expressed as $CrO_xF_y$. However, the correlation between the particular chromium species which may be present in such catalysts and their catalytic activity in fluorination reactions has not been well understood. For example, two catalysts with substantially identical empirical compositions (i.e., catalysts having the same content of Cr, O, F and other elements that may be present) may be quite different in catalytic performance. This has made it challenging to manufacture chromium oxyfluoride catalysts with desirably high levels of activity and to regenerate used chromium oxyfluoride catalysts to improve or restore their activity.

Accordingly, the development of analytical methods which are capable of readily and accurately predicting the catalytic performance of chromium oxyfluoride compositions in fluorination reactions would be of great interest.

SUMMARY OF THE INVENTION

It has now been discovered that X-ray photoelectron spectroscopy (XPS) methods can be utilized to characterize chromium oxyfluoride catalysts and reliably forecast their activity in catalyzing the fluorination of chlorinated compounds.

One aspect of the invention provides a chromium oxyfluoride catalyst active for fluorination of a chlorinated compound, wherein the chromium oxyfluoride catalyst is comprised of a first chromium species and a second chromium species, wherein the first chromium species exhibits a first X-ray photoelectron spectroscopy (XPS) chromium Cr $2p^{3/2}$ peak between 576.9 eV+/−0.2 eV and 578.0 eV+/−0.2 eV and the second chromium species exhibits a second X-ray photoelectron spectroscopy (XPS) chromium Cr $2p^{3/2}$ peak between 580.0 eV+/−0.2 eV and 581.4 eV+/−0.2 eV and wherein the intensity of the second XPS chromium peak is greater than the intensity of the first XPS chromium peak.

In one desirable embodiment of the invention, the energy shift between the first XPS chromium Cr $2p^{3/2}$ peak and the second XPS chromium Cr $2p^{3/2}$ peak is 3.3 eV±1.7 eV.

The chromium oxyfluoride catalyst may be a supported catalyst, for example a catalyst supported on an aluminum-containing support. In another embodiment, the chromium oxyfluoride catalyst may be a bulk (unsupported) catalyst.

When the catalyst is a supported catalyst, the ratio of the intensity of the second XPS chromium Cr $2p^{3/2}$ peak to the intensity of the first XPS chromium Cr $2p^{3/2}$ peak is advantageously greater than 2.5 in one embodiment of the invention.

When the chromium oxyfluoride catalyst is a bulk catalyst, the ratio of the intensity of the second XPS chromium Cr $2p^{3/2}$ peak to the intensity of the first XPS chromium Cr $2p^{3/2}$ peak is, in various embodiments, advantageously greater than 6.0, greater than 7.0 or greater than 8.0.

In a further aspect of the invention, the chromium oxyfluoride catalyst is further comprised of a first oxygen species and a second oxygen species, wherein the first oxygen species exhibits a first X-ray photoelectron spectroscopy (XPS) oxygen O 1 s peak between 530.3 eV±0.2 eV and 531.6 eV±0.2 eV and the second oxygen species exhibits a second X-ray photoelectron spectroscopy (XPS) oxygen O 1 s peak between 532.4 eV±0.2 eV and 532.8 eV±0.2 eV and wherein the intensity of the second XPS oxygen O 1 s peak is greater than the intensity of the first XPS oxygen O 1 s peak. For example, the ratio of the intensity of the second XPS oxygen O 1 s peak to the intensity of the first XPS oxygen O 1 s peak may be greater than 2.

In addition to Cr, O and F, the chromium oxyfluoride catalyst may contain one or more further elements, such as a transition metal. For example, the chromium oxyfluoride catalyst may be nickel-modified.

Also provided by the present invention is a method of assessing the activity of a chromium oxyfluoride catalyst for fluorination of a chlorinated compound, wherein the method comprises analyzing the chromium oxyfluoride catalyst by X-ray photoelectron spectroscopy (XPS) to measure the relative intensities of a first chromium Cr $2p^{3/2}$ peak between 576.9 eV+/−0.2 eV and 578.0 eV+/−0.2 eV associated with a first chromium species and a second chromium Cr $2p^{3/2}$ peak between 580.0 eV+/−0.2 eV and 581.4 eV+/−0.2 eV associated with a second chromium species.

In yet another embodiment of the invention, a method of fluorinating a chlorinated compound is provided, comprising contacting the chlorinated compound and hydrogen fluoride in gas phase in the presence of a chromium oxyfluoride catalyst in accordance with any of the above-described embodiments to produce a fluorinated compound.

A still further embodiment of the invention furnishes a method of making a chromium oxyfluoride catalyst active for fluorination of a chlorinated compound, wherein the method comprises preparing the chromium oxyfluoride catalyst under conditions effective to provide a chromium oxyfluoride catalyst wherein the intensity of a first XPS chromium Cr $2p^{3/2}$ peak between 576.9 eV+/−0.2 eV and 578.0 eV+/−0.2 eV associated with a first chromium species in the chromium oxyfluoride catalyst is less than the intensity of a second XPS chromium Cr $2p^{3/2}$ peak between 580.0 eV+/−0.2 eV and 581.4 eV+/−0.2 eV associated with a second chromium species. Such method may comprise, for example, the following stages, in succession: a) an unactivated catalyst preparation stage, wherein an unactivated chromium oxyfluoride catalyst is prepared; b) a first activation stage, wherein the unactivated chromium oxyfluoride catalyst is subjected to activation conditions to obtain a first activated chromium oxyfluoride catalyst; c) a catalyst evaluation stage, wherein the first activated chromium oxyfluoride catalyst is analyzed by XPS to measure the relative intensities of a first XPS chromium Cr $2p^{3/2}$ peak between 576.9 eV+/−0.2 eV and 578.0 eV+/−0.2 eV and a second XPS chromium Cr $2p^{3/2}$ peak between 580.0 eV+/−0.2 eV and 581.4 eV+/−0.2 eV; and either d1) a second activation stage, wherein the first activated chromium oxyfluoride catalyst is further subjected to activation conditions to obtain a second activated chromium oxyfluoride catalyst, if the intensity of the first XPS chromium Cr $2p^{3/2}$ peak is not less than the intensity of the second XPS chromium Cr $2p^{3/2}$ peak or d2) a reaction stage wherein a chlorinated compound is contacted with hydrogen fluoride in gas phase in the presence of the first activated chromium oxyfluoride catalyst to produce a fluorinated compound, if the intensity of the first XPS chromium Cr $2p^{3/2}$ peak is less than the intensity of the second XPS chromium Cr $2p^{3/2}$ peak.

A method of regenerating a spent chromium oxyfluoride catalyst to improve its activity for fluorination of a chlorinated compound is provided in another embodiment of the invention, wherein the method comprises regenerating the chromium oxyfluoride catalyst under conditions effective to provide a chromium oxyfluoride catalyst wherein the intensity of a first XPS chromium Cr $2p^{3/2}$ peak between 576.9 eV+/−0.2 eV and 578.0 eV+/−0.2 eV associated with a first chromium species present in the chromium oxyfluoride catalyst is less than the intensity of a second XPS chromium Cr $2p^{3/2}$ peak between 580.0 eV+/−0.2 eV and 581.4 eV+/−0.2 eV associated with a second chromium species. For example, a fluorination process may be conducted comprising the following steps in succession: a) a first reaction stage wherein a chlorinated compound is contacted with hydrogen fluoride in gas phase in the presence of a chromium oxyfluoride catalyst to produce a fluorinated compound, wherein the first reaction stage is carried out for a length of time sufficient to cause the activity of the chromium oxyfluoride catalyst to fall below a selected value; b) a first reactivation stage, wherein the chromium oxyfluoride catalyst is subjected to reactivation conditions to obtain a first reactivated chromium oxyfluoride catalyst; c) a catalyst evaluation stage, wherein the first reactivated chromium oxyfluoride catalyst is analyzed by XPS to measure the relative intensities of a first XPS chromium Cr $2p^{3/2}$ peak between 576.9 eV+/−0.2 eV and 578.0 eV+/−0.2 eV and a second XPS chromium Cr $2p^{3/2}$ peak between 580.0 eV+/−0.2 eV and 581.4 eV+/−0.2 eV; and either d1) a second reactivation stage, wherein the chromium oxyfluoride catalyst is further subjected to reactivation conditions to obtain a second reactivated chromium oxyfluoride catalyst, if the intensity of the first XPS chromium Cr $2p^{3/2}$ peak is not less than the intensity of the second XPS chromium Cr $2p^{3/2}$ peak or d2) a second reaction stage wherein a chlorinated compound is contacted with hydrogen fluoride in gas phase in the presence of the first reactivated chromium oxyfluoride catalyst to produce a fluorinated compound, if the intensity of the first XPS chromium Cr $2p^{3/2}$ peak is less than the intensity of the second XPS chromium Cr $2p^{3/2}$ peak.

DETAILED DESCRIPTION OF THE INVENTION

Any of the starting materials and processing methods known in the art of chromium oxyfluoride catalysts may be adapted for use in making chromium oxyfluoride catalysts in accordance with the present invention.

The catalyst comprises at least chromium, oxygen, and fluorine. However, the catalyst may also comprise one or more additional elements, for example one or more metals in addition to chromium. In one embodiment, the catalyst is comprised of Cr, O, F and at least one co-catalyst selected from the group consisting of Zn, Co, Ni, Mn, Mg and combinations thereof. The chromium oxyfluoride catalyst may be supported or unsupported.

A commercial chromium fluoride compound may be used as a precursor to the chromium oxyfluoride catalyst. Any suitable chromium fluoride compound may be selected, such as $CrF_3 \cdot xH_2O$, $Cr/Ni/AlF_3$, fluorided $Cr_2O_3$, and the like. The chromium fluoride compound may be anhydrous or hydrated. The chromium fluoride compound, such as $CrF_3 \cdot xH_2O$, may first be calcined. The calcination may occur under any suitable conditions. For example, during the calcination, the chromium fluoride compound may be heated to a temperature between about 200-1000° C., e.g., between about 400-500° C. The chromium fluoride may be heated up in a stream or atmosphere of at least one inert gas, such as nitrogen, helium, or argon. In an exemplary embodiment, the chromium fluoride is heated in a stream of nitrogen to calcine the catalyst precursor. It is also possible to calcine the hydrated chromium fluoride using an active gas (e.g., a gas capable of reacting, such as air). The inert gas or active gas may be pre-heated or the reactor may be heated once the catalyst precursor and the inert gas or active gas are contained therein. A contact time between the heated inert gas or active gas and the catalyst precursor may be about 10-200 seconds, preferably 10-100 seconds, more preferably about 20-50 seconds. The operating pressure is not particularly critical and may be between atmospheric and lower vacuum, e.g., 1-10 mmHg.

In an exemplary embodiment, the catalyst is formed by calcining $CrF_3 \cdot xH_2O$, where x is 1-10, or more preferably x is 3-5, to form a calcined chromium oxyfluoride. In one embodiment, the catalyst is formed by calcination of chromium (III) fluoride tetrahydrate where x equals 4 (i.e., $CrF_3 \cdot 4H_2O$).

Without wishing to be bound by theory, it is believed that the calcination of the chromium fluoride using an inert gas, such as nitrogen, or active gas, such as air, proceeds by a dehydration step and a hydrolysis step to form the chromium oxyfluoride catalyst. The following reaction schemes may be representative of the (1) dehydration and (2) hydrolysis steps, it being understood that chromium oxyfluoride species other than or in addition to CrOF may be formed:

$$CrF_3 \cdot 4H_2O \rightarrow CrF_3 \cdot H_2O + 3H_2O \quad (1)$$

$$CrF_3 \cdot H_2O \rightarrow CrOF + 2HF \quad (2)$$

The calcined chromium oxyfluoride may optionally be activated with HF (or another source of reactive fluorine, such as $F_2$ or $NF_3$) after calcination. However, in other embodiments the catalyst is not activated with hydrogen fluoride or other fluorine source. The calcined chromium oxyfluoride catalyst may be directly used in fluorination or may undergo further processing, such as pelletizing.

In another embodiment, the catalyst is formed by activating a chromium- and oxygen-containing compound (e.g., a chromium oxide), such as $Cr_2O_3$, with a reactive fluorine source such as hydrogen fluoride, $F_2$ or $NF_3$ to form an activated chromium oxyfluoride. The activation may be represented by the following reaction involving HF as the fluorine source (once again, CrOF may not be the only chromium oxyfluoride species formed):

$$Cr_2O_3 + 2HF \rightarrow 2CrOF + H_2O$$

Thus, the catalyst or its precursor may undergo a hydrogen fluoride, $F_2$ and/or $NF_3$ activation based on the starting catalyst material selected.

The catalyst may be unsupported or supported. When supported, the catalyst may be supported using one or more suitable supports, such as activated carbon, graphite, chromia, alumina, zirconia, titania, magnesia, or their corresponding HF-activated compounds, such as fluorinated graphite, fluorinated chromia, fluorinated alumina, etc. In an exemplary embodiment, the catalyst comprises at least one support selected from the group consisting of alumina, fluorinated alumina, chromia, fluorinated chromia, activated carbon, HF-activated carbon, and mixtures thereof. In a particular embodiment, the chromium oxyfluoride is supported on alumina. When the catalyst is supported, it is suitable that the amount of chromium carried thereon is about 1-20 total wt %, e.g., about 5-10 total wt %. The catalyst does not require a co-catalyst in addition to chromium, but one or more co-catalysts (sometimes referred to as dopants), such as Co, Zn, Mn, Mg, V, Mo, Te, Nb, Sb, Ta, P, Ni, Ca, Sr, Ba, Na, K, Rb, Cs, Cd, Hg, Cu, Ag, Au, Pd, Pt, W, Ti, Zr, Hf or combinations thereof, may be included therewith, typically in a total amount of up to about 10% by weight of the catalyst. According to one embodiment, the chromium oxyfluoride catalyst is a mixed chromium/nickel catalyst, the atomic ratio of nickel to chromium being from 0.5 to 2 in one embodiment and approximately 1 in another embodiment.

In one embodiment, the catalyst is obtained by calcination of a precursor mixture comprising chromium, nickel, and $AlF_3$. The catalyst may be a mixed chromium/nickel catalyst, in particular a supported mixed chromium/nickel catalyst, the atomic ratio of nickel to chromium being, for example, from 0.5 to 2 (e.g., about 1). The catalyst may contain from 0.5 to 20% by weight chromium (e.g., between 2 and 10% by weight Cr) and from 0.5 to 20% by weight nickel (e.g., between 2 and 10% by weight Ni). Such catalysts may be made, for example, by impregnating a suitable support, such as alumina fluoride, with solutions of a soluble nickel salt and a soluble chromium compound, such as chromic anhydride ($CrO_3$), drying the impregnated support and then calcining at a temperature of, for example, 300° C. and 400° C. (in the presence of an oxidizing agent, such as oxygen, and/or HF). The catalyst thus obtained may then be subjected to an activation step, under conditions effective to provide an activated catalyst having XPS peak characteristics in accordance with the present invention. The activation step may involve contacting the catalyst with a source of reactive fluorine, such as HF, $F_2$ and/or $NF_3$. The contacting may be carried out in a gas (vapor) phase at a temperature of about 100° C. to about 400° C., for example. Methods of activating chromium oxyfluoride catalysts using sources of reactive fluorine are described, for example, in WO 2014/120493, the disclosure of which is incorporated herein by reference in its entirety for all purposes.

The physical shape of the catalyst is not particularly limited. In one embodiment, the catalyst is in the shape of pellets, beads or granules. The catalyst may be combined with other ingredients, such as graphite, which may function as a bonding agent for making stronger pellets and/or to operate under pressure without attrition. Additionally, for supported catalysts, the supports may also be in the form of granules or pellets, or the like. In an exemplary embodiment, the catalyst is pelletized and the pellet size is between about 1/16" to 1/4", depending on the reactor diameter. It is contemplated that the amount of catalyst used will vary depending on the particular parameters present during the fluorination reaction, which could be readily ascertainable by one of ordinary skill in the art. Other ingredients may also be added to the catalyst for use in the reactor, such as a bonding agent. For example, about 1-5 weight % of a bonding agent, such as graphite or alumina, may be used.

The starting materials and processing/activation conditions used to prepare the chromium oxyfluoride catalyst are selected and controlled so as to provide a catalyst comprised of a first chromium species and a second chromium species, wherein the first chromium species exhibits a first X-ray photoelectron spectroscopy (XPS) chromium Cr $2p^{3/2}$ peak between 576.9 eV+/−0.2 eV and 578.0 eV+/−0.2 eV and the second chromium species exhibits a second X-ray photoelectron spectroscopy (XPS) chromium Cr $2p^{3/2}$ peak between 580.0 eV+/−0.2 eV and 581.4 eV+/−0.2 eV and wherein the intensity of the second XPS chromium peak is greater than the intensity of the first XPS chromium peak.

Without wishing to be bound by theory, it is believed that the lower binding energy chromium form (referred to herein as the "first chromium species") is a low fluorinated form of chromium oxohydroxide, having a proposed chemical formula $CrO(OH)_xF_{1-x}$, with x varying as a function of the degree of surface fluorination. Regardless of the value of x, however, the chromium is believed to have an oxidation state of +3 in the first chromium species. It is additionally thought (again, without wishing to be bound by theory) that the second chromium species likely corresponds to one (or more) of the following formulae (the species appearing in bold are thought to be the most likely forms of catalytically active chromium):

Cr(III): CrOF; $Cr(OH)F_2$; $CrO_{0.5}F_2$
Cr(IV): $CrF_4$; $CrOF_2$; $Cr(OH)F_3$
Cr(V): $CrO_2F$; $CrOF_3$; $CrO_{0.5}F_4$

The empirical formula of the second (more active) chromium species may be expressed as $CrO_xF_y$, wherein x varies from 0.5 to 2.0 and y varies from 1.0 to 4.0

XPS analyses of active and deactivated chromium oxyfluoride catalysts clearly show that high or dominant levels of the second chromium species, relative to the first chromium species, are necessary in order for the catalyst to have strong catalytic activity in fluorination reactions. Surface chemistry quantification has been used to establish that highly active catalysts have high fluorine to oxygen ratios at their surfaces, consistent with the observation that many of the above-mentioned possible second chromium species have high fluorine to oxygen ratios.

The following X-ray photoelectron spectroscopy (XPS) procedures are utilized to determine whether a particular chromium oxyfluoride composition has XPS characteristics in accordance with the present invention. Surface elemental analysis is performed using a Thermo Scientific K-alpha XPS spectrometer which is calibrated using a three point calibration (Au, Ag, Cu). The analysis is carried out using a 200-400 m beam spot size generated by a monochromatic aluminum source having an energy of 1486.6 eV, a pass energy of 50 eV, a step size of 0.1 eV, and a counting time of 50 to 100 ms/step. Typically, at least twenty scans are recorded for each spectrum.

A further description of the XPS procedures is as follows:
X-ray source: Al K alpha monochromatized source (1486.68 eV), 12 kV, 3.3 mA. Photoelectron collection system includes hemispherical analyzer and 128 channel detectors. Micro-focus monochromatized beam typically used with a beam spot size of 250 μm. Sample charge neutralization performed with dual low energy electron flood gun and ion flood source. Energy scale calibrated with a three point calibration curve (Au $4f^{7/2}$, Ag $3d^{5/2}$, Cu $2p^{3/2}$).

Chromium peak data collection: Cr 2p lines and shake up lines from 565 eV to 630 eV.
Typically at least 20 scans collected with a 50 eV pass energy, 0.1 eV step, 50 ms/step.
The following procedure for peak decomposition is used to obtain information regarding chromium forms 1 and 2 (peak positions and relative peak intensities). To clarify, the ratio of chromium form 2 to chromium form 1 is based on the ratio of peak intensities of peak 2 and peak 1, not the ratio of peak areas of peak 2 and peak 1.
  a) Background for peak integration: Shirley type background or "Smart" background as used in Thermo Avantage software.
  b) Chromium lines peak fitting using a mixed Lorentzian/Gaussian function (mix value=30%). For reference if mix value is 0% the function is purely Gaussian, if mix value is 100% the function is purely Lorentzian).
  c) Doublet line separation (Cr $2p^{3/2}$-Cr $2p^{1/2}$) constrained at 9.4 eV±0.5 eV and intensity ratio of the doublet Cr $2p^{1/2}$/Cr $2p^{3/2}$ constrained at 0.512±0.1.
  d) Doublet full width at half maximum (FWHM) constrained at 1.0 eV to 3.5 eV for Cr $2p^{3/2}$ and FWHM of Cr $2p^{1/2}$ typically constrained to that of Cr $2p^{3/2}$±0.5 eV,
  e) Chi-square achieved in refinement typically better than 4.

If the composition is analyzed in pellet or bead form, the pellet or bead is attached to an XPS aluminum stub with double-sided carbon tape. The composition may alternatively be analyzed in powder form (if the composition is initially in the form of a pellet or bead, the pellet or bead is crushed using a mortar and pestle). When the catalyst is a catalyst supported on an Al-containing support, the XPS measurements are charge referenced to aluminum (Al 2p at 76.90 eV). Alternatively, if the catalyst is not supported on an Al-containing support, charge referencing can be done by referencing the carbon spectrum to the alkyl peak at 285.0 eV, or by using one of the catalyst doping materials such as zinc by referencing at 1023.2 eV. As the samples are typically electrically insulating, a flood gun emitting low energy electrons is used for partial charge compensation on the sample surface.

Chromium oxyfluoride catalysts having the XPS characteristics described herein may be used generally in fluorination reactions, in particular fluorination reactions wherein a chlorinated compound is reacted with a source of fluorine such as HF. Such reactions are carried out under conditions effective to replace one or more or all of the chlorine atoms initially present in the chlorinated compound with fluorine atoms, with the chromium oxyfluoride catalyzing such reaction. For example, the chlorinated compound may be a chloroolefin containing one or more Cl atoms. Halogenated C3 compounds, which may be saturated or unsaturated, containing at least one chlorine atom and optionally one or more fluorine atoms per molecule may be used in such a reaction, for example. Exemplary halogenated C3 compounds suitable for such purposes include, for example, 1,1,2,3-tetrachloropropene, 1,1,1,2,3-pentachloropropane, 2,3,3,3-tetrachloropropene, 2-chloro-3,3,3-trifluoropropene (HCFO-1233xf), 2,3-dichloro-1,1,1-trifluoropropane (HCFC-243db) and the like. In a particularly advantageous embodiment of the invention, the chromium oxyfluoride catalyst is utilized as a catalyst in a reaction wherein 2-chloro-3,3,3-trifluoropropene is converted to 2,3,3,3-tetrafluoropropene (HFO-1234yf).

In various embodiments of the invention, a batch of chromium oxyfluoride catalyst may be prepared and a sample analyzed by XPS to determine if it possesses the characteristics associated with a high degree of fluorination activity as described elsewhere herein. If the XPS analysis indicates that the batch does have such characteristics, then the chromium oxyfluoride catalyst is subsequently used in a fluorination reaction wherein, for example, a chlorinated compound is contacted with HF or other source of fluorine under conditions effective to achieve at least partial replacement of Cl in the chlorinated compound with F. If, on the other hand, such XPS analysis shows that the batch of chromium oxyfluoride catalyst lacks the characteristics of a high activity fluorination catalyst, then such batch is discarded or perhaps reprocessed or re-activated, rather than being employed in a fluorination production operation.

Thus, the XPS techniques described herein provide a convenient, rapid method of determining whether a given batch of chromium oxyfluoride catalyst will perform satisfactorily, thereby avoiding the need to actually charge the batch to a reactor and contact the catalyst with HF and a chlorinated compound in order to assess its activity.

Similarly, if a batch of chromium oxyfluoride catalyst which has been used in a fluorination process for a period of time is found to have lost activity and is therefore subjected to one or more regeneration steps for the purpose of reactivating the catalyst, the present invention furnishes a way of determining, without having to restart the fluorination process, whether the regenerated catalyst is likely to have a desired minimum level of activity. That is, a sample of the catalyst which has been subjected to a regeneration procedure may be analyzed by XPS to assess whether the relative intensities of the XPS peaks associated with the first and second chromium species meet the requirements set forth herein (e.g., the intensity of the second XPS chromium peak is greater than the intensity of the first XPS chromium peak). Reactivation of a catalyst may involve, for example, heating a deactivated catalyst in the presence of oxygen (e.g., calcining the deactivated catalyst in air) followed by contacting the catalyst with a source of reactive fluorine (e.g., treatment with HF, $F_2$ and/or $NF_3$). Alternatively, the deactivated catalyst can be contacted directly with a source of reactive fluorine, without an initial heating step in the presence of oxygen. In yet another embodiment, reactivation is accomplished by first contacting the deactivated catalyst with a source of reactive fluorine, then with a source of oxygen such as air. Such contacting/heating steps may be carried out at temperatures of from about 100° C. to about 500° C., for example. Catalyst regeneration (reactivation) techniques are described, for example, in US Pat. Pub. No. 2014/0012051 and WO 2014/120493, the disclosure of each of which is incorporated herein by reference in its entirety for all purposes.

Re-activation is necessary not so much for the removal of coke that has accumulated on the catalyst, but to re-organize the chromium structure by converting at least a portion of the first chromium species (having lower catalytic activity) to the second chromium species (having higher catalytic activity). This re-activation may involve, in a first step, oxidizing the chromium using oxygen. The second step of catalyst re-activation may occur when the fluorination reaction is re-started and either HF and/or fluoro-olefin is contacted with the catalyst surface, thereby completing catalyst re-activation and increasing the proportion of the second chromium species relative to the first chromium species.

The chromium oxyfluoride catalysts of the present invention are generally useful for catalyzing the fluorination of chlorinated compounds, wherein one or more of the Cl atoms in the starting material are replaced by fluorine. Typically, a source of fluorine, such as HF, is contacted with the chlorinated compound in the presence of the chromium oxyfluoride catalyst. Accordingly, the chromium oxyfluoride catalyst may be used in a fluorination process, comprising a reaction stage, wherein the reaction stage comprises reacting a chlorinated compound with hydrogen fluoride in a gas phase in the presence of the catalyst to produce a fluorinated compound. The fluorination process may optionally additionally comprise a regeneration stage which comprises contacting the catalyst, after it has been used in a reaction stage, with an oxidizing agent-containing gas flow. Multiple alternating reaction stages and regeneration stages may be employed in such a fluorination process.

According to one embodiment, the fluorination process comprises a preliminary activation stage which comprises contacting the catalyst with an oxidizing agent-containing gas flow. However, in another embodiment, the catalyst is not contacted with an oxidizing agent during activation.

According to one embodiment, the oxidizing agent-containing gas flow of the activation stage and/or the regeneration stage(s) is an oxygen-containing gas flow.

According to one embodiment, the activation stage and/or the regeneration stage(s) comprise contacting the catalyst with the oxidizing agent-containing gas flow for at least 2 hours, preferably for at least 4 hours, more preferably for at least 10 hours, and even more preferably for at least 15 hours.

According to one embodiment, the oxidizing agent-containing gas flow of the activation stage and/or the regeneration stage(s) contains hydrogen fluoride in addition to the oxidizing agent, and the proportion of oxidizing agent in the oxidizing agent-containing gas flow of the activation stage and/or the regeneration stage(s) is preferably from 2 to 98 mol %, and more preferably from 5 to 50 mol %, relative to the total amount oxidizing agent and hydrogen fluoride.

According to one embodiment, the oxidizing agent-containing gas flow of the activation stage and/or the regeneration stage(s) does not contain hydrogen fluoride, and preferably is air, oxygen, or a blend of oxygen with one or more other gases.

According to one embodiment, the activation stage and/or the regeneration stage(s) comprise contacting the catalyst with a hydrogen fluoride gas flow, either before contacting the catalyst with the oxidizing agent-containing gas flow or after contacting the fluorination catalyst with the oxidizing agent-containing gas flow.

According to one embodiment, the activation stage comprises a preliminary step of reacting the chlorinated compound with hydrogen fluoride in gas phase in the presence of the fluorination catalyst, prior to contacting the chlorinated compound with the oxidizing agent-containing gas flow.

According to one embodiment, the oxidizing agent-containing gas flow is contacted with the fluorination catalyst during the activation stage and/or the regeneration stage(s) at a temperature of from 250 to 500° C., preferably from 300 to 400° C., more preferably from 350 to 380° C.

The fluorinated compound may be a C2 or C3 or C4 or C5 alkane or alkene compound (preferably alkene), which is linear or branched (preferably linear), having one or more substituents selected from F, Cl, I and Br (preferably from F and Cl), at least one of the substituents being F. According to one embodiment, the fluorinated compound produced in the fluorination process is a fluoroolefin (in one embodiment, containing no chlorine), in particular a fluoropropene, such as 2,3,3,3-tetrafluoro-1-propene.

According to one embodiment, the chlorinated compound is selected from hydrochlorocarbons, hydrochlorofluorocarbons and hydrochlorofluoroolefins. For example, the chlorinated compound may be a C2 or C3 or C4 or C5 alkane or alkene compound, which is linear or branched, having one or more substituents selected from F, Cl, I and Br, at least one of the substituents being Cl. Examples of suitable chlorinated compounds include, but are not limited to, 2-chloro-3,3,3-trifluoro-1-propene, 1,1,1,2,3-pentachloropropane, 1,1,2,2,3-pentachloropropane, 2,3-dichloro-1,1,1-trifluoropropane, 2,3,3,3-tetrachloro-1-propene and 1,1,2,3 tetrachloro-1-propene.

Where the chlorinated compound is 2-chloro-3,3,3-trifluoro-1-propene, according to one embodiment, the molar ratio of hydrogen fluoride to 2-chloro-3,3,3-trifluoro-1-propene may be from 1:1 to 150:1, e.g., 2:1 to 70:1, 3:1 to 50:1, or 5:1 to 30:1.

According to one embodiment, the reaction stage(s) may be carried out at a pressure of from 0.1 to 20 bars, e.g., from 1 to 15 bars or from 3 to 10 bars.

According to one embodiment, the reaction stage(s) may be carried out at a temperature of from 200 to 450° C., e.g., from 300 to 430° C., from 320 to 420° C. or from 340 to 390° C.

According to one embodiment, the contact time between hydrogen fluoride and the chlorinated compound during the reaction stage(s) may be from 2 to 100 s, e.g., from 5 to 80 s or from 7 to 50 s. During the reaction, in one embodiment of the invention, at least one Cl substituent in the chlorinated compound is replaced by an F substituent.

The conversion of the chlorinated compound to the fluorinated compound may comprise direct conversion (i.e. in a single reaction step or under essentially one set of reaction conditions) or indirect conversion (i.e., through two or more reaction steps or using more than one single set of reaction conditions).

For example, the chromium oxyfluoride catalysts described herein may be utilized in processes wherein 2,2,2,3-tetrafluoropropene (HFO-1234yf) is produced from 2-chloro-3,3,3-trifluoropropene (HCFO-1233xf) or 1,1,1,2,3-pentachloropropane, as described in US Pat. Pub. Nos. 2014/0039228 and 2014/012051, each of which is incorporated herein by reference in its entirety for all purposes.

The present invention comprises:
1. A chromium oxyfluoride catalyst active for fluorination of a chlorinated compound, wherein the chromium oxyfluoride catalyst is comprised of a first chromium species and a second chromium species, wherein the first chromium species exhibits a first X-ray photoelectron spectroscopy (XPS) chromium Cr $2p^{3/2}$ peak between 576.9 eV+/−0.2 eV and 578.0 eV+/−0.2 eV and the second chromium species exhibits a second X-ray photoelectron spectroscopy (XPS) chromium Cr $2p^{3/2}$ peak between 580.0 eV+/−0.2 eV and 581.4 eV+/−0.2 eV and wherein the intensity of the second XPS chromium peak is greater than the intensity of the first XPS chromium peak.
2. The chromium oxyfluoride catalyst of claim 1, wherein the chromium oxyfluoride catalyst is a supported catalyst.
3. The chromium oxyfluoride catalyst of any one of the preceding claims, wherein the chromium oxyfluoride catalyst is a catalyst supported on an aluminum-containing support.
4. The chromium oxyfluoride catalyst of any one of the preceding claims, wherein the ratio of the intensity of the second XPS chromium peak to the intensity of the first XPS chromium peak is greater than 2.5.
5. The chromium oxyfluoride catalyst of claim 1, wherein the chromium oxyfluoride catalyst is a bulk catalyst.
6. The chromium oxyfluoride catalyst of any one of claims 1 and 5, wherein the ratio of the intensity of the second XPS chromium peak to the intensity of the first XPS chromium peak is greater than 8.0.
7. The chromium oxyfluoride catalyst of any one of the preceding claims, wherein the chromium oxyfluoride catalyst is comprised of a first oxygen species and a second oxygen species, wherein the first oxygen species exhibits a first X-ray photoelectron spectroscopy (XPS) oxygen O 1 s peak between 530.3 eV±0.2 eV and 531.6 eV±0.2 eV and the second oxygen species exhibits a second X-ray photoelectron spectroscopy (XPS) oxygen O 1 s peak between 532.4 eV±0.2 eV and 532.8 eV±0.2 eV and wherein the intensity of the second XPS oxygen peak is greater than the intensity of the first XPS oxygen peak.
8. The chromium oxyfluoride catalyst of any one of the preceding claims, wherein the ratio of the intensity of the second XPS oxygen O 1 s peak to the intensity of the first XPS oxygen O 1 s peak is greater than 2.
9. The chromium oxyfluoride catalyst of any one of the preceding claims, wherein the energy shift between the first XPS chromium Cr $2p^{3/2}$ peak and the second XPS chromium Cr $2p^{3/2}$ peak is 3.3 eV±1.7 eV.
10. The chromium oxyfluoride catalyst of any one of the preceding claims, wherein the chromium oxyfluoride catalyst is modified with at least one metal selected from the group consisting of Zn, Co, Ni, Mn, Mg and combinations thereof.
11. A method of assessing the activity of a chromium oxyfluoride catalyst for fluorination of a chlorinated compound, wherein the method comprises analyzing the chromium oxyfluoride catalyst by X-ray photoelectron spectroscopy (XPS) to measure the relative intensities of a first XPS chromium Cr $2p^{3/2}$ peak between 576.9 eV+/−0.2 eV and 578.0 eV+/−0.2 eV associated with a first chromium species and a second XPS chromium Cr $2p^{3/2}$ peak between 580.0 eV+/−0.2 eV and 581.4 eV+/−0.2 eV associated with a second chromium species.
12. A method of fluorinating a chlorinated compound, comprising contacting the chlorinated compound and hydrogen fluoride in gas phase in the presence of a chromium oxyfluoride catalyst in accordance with any one of claims 1-10 to produce a fluorinated compound.
13. The method of claim 12, wherein the chlorinated compound is 1,1,2,3-tetrachloropropene and the fluorinated compound is HFO-1234yf or the chlorinated compound is 2-chloro-3,3,3-trifluoropropene and the fluorinated compound is HFO-1234yf.
14. A method of making a chromium oxyfluoride catalyst active for fluorination of a chlorinated compound, wherein the method comprises preparing the chromium oxyfluoride catalyst under conditions effective to provide a chromium oxyfluoride catalyst wherein the intensity of a first XPS chromium Cr $2p^{3/2}$ peak between 576.9 eV+/−0.2 eV and 578.0 eV+/−0.2 eV associated with a first chromium species in the chromium oxyfluoride catalyst is less than the intensity of a second XPS chromium Cr $2p^{3/2}$ peak between 580.0 eV+/−0.2 eV and 581.4 eV+/−0.2 eV associated with a second chromium species.
15. A method of making a chromium oxyfluoride catalyst active for fluorination of a chlorinated compound, comprising the following stages, in succession: a) an unactivated catalyst preparation stage, wherein an unactivated chromium oxyfluoride catalyst is prepared; b) a first activation stage, wherein the unactivated catalyst is subjected to activation conditions to obtain a first activated chromium oxyfluoride catalyst; c) a catalyst evaluation stage, wherein the first activated chromium oxyfluoride catalyst is analyzed by XPS to measure the relative intensities of a first XPS chromium Cr $2p^{3/2}$ peak between 576.9 eV+/−0.2 eV and 578.0 eV+/−0.2 eV and a second XPS chromium Cr $2p^{3/2}$ peak between 580.0 eV+/−0.2 eV and 581.4 eV+/−0.2 eV; and either d1) a second activation stage, wherein the first activated chromium oxyfluoride catalyst is further subjected to activation conditions to obtain a second activated chromium oxyfluoride catalyst, if the intensity of the first XPS chromium Cr $2p^{3/2}$ peak is not less than the intensity of the second XPS chromium Cr $2p^{3/2}$ peak or d2) a reaction stage wherein a chlorinated compound is contacted with hydrogen fluoride in gas phase in the presence of the first activated chromium oxyfluoride catalyst to produce a fluorinated compound, if the intensity of the first XPS chromium Cr $2p^{3/2}$ peak is less than the intensity of the second XPS chromium Cr $2p^{3/2}$ peak.
16. A method of regenerating a spent chromium oxyfluoride catalyst to improve its activity for fluorination of a chlorinated compound, wherein the method comprises regenerating the chromium oxyfluoride catalyst under conditions effective to provide a chromium oxyfluoride catalyst wherein the intensity of a first XPS chromium Cr $2p^{3/2}$ peak between 576.9 eV+/−0.2 eV and 578.0 eV+/−0.2 eV associated with a first chromium species present in the chromium oxyfluoride catalyst is less than the intensity of a second XPS chromium Cr $2p^{3/2}$ peak between 580.0 eV+/−0.2 eV and 581.4 eV+/−0.2 eV associated with a second chromium species.
17. A method, comprising the following steps in succession: a) a first reaction stage wherein a chlorinated compound is contacted with hydrogen fluoride in gas phase in the presence of a chromium oxyfluoride catalyst to produce a fluorinated compound, wherein the first reaction stage is carried out for a length of time sufficient to cause the activity of the chromium oxyfluoride catalyst to fall below a selected value; b) a first reactivation stage, wherein the chromium oxyfluoride catalyst is subjected to reactivation conditions to obtain a first reactivated chromium oxyfluoride catalyst; c) a catalyst evaluation stage, wherein the first reactivated chromium oxyfluoride catalyst is analyzed by XPS to measure the relative intensities of a first XPS chromium Cr $2p^{3/2}$ peak between 576.9 eV+/−0.2 eV and 578.0 eV+/−0.2 eV and a second XPS chromium Cr $2p^{3/2}$ peak between 580.0 eV+/−0.2 eV and 581.4 eV+/−0.2 eV; and either d1) a second reactivation stage, wherein the chromium oxyfluoride catalyst is further subjected to reactivation conditions to obtain a second reactivated chromium oxyfluoride catalyst, if the intensity of the first XPS chromium Cr $2p^{3/2}$ peak is not less than the intensity of the second XPS chromium Cr $2p^{3/2}$ peak or d2) a second reaction stage wherein a chlorinated compound is contacted with hydrogen fluoride in gas phase in the presence of the first reactivated chromium oxyfluoride catalyst to produce a fluorinated compound, if the intensity of the first XPS chromium Cr $2p^{3/2}$ peak is less than the intensity of the second XPS chromium Cr $2p^{3/2}$ peak.

Within this specification embodiments have been described in a way which enables a clear and concise specification to be written, but it is intended and will be appreciated that embodiments may be variously combined or separated without parting from the invention. For example, it will be appreciated that all preferred features described herein are applicable to all aspects of the invention described herein

EXAMPLES

Data Collection and Peak Decomposition Procedure:

Experimental work performed with a Thermo K-Alpha spectrometer. X-ray source: Al K alpha monochromatized source (1486.68 eV), 12 kV, 3.3 mA. Photoelectron collection system includes hemispherical analyzer and 128 channel detectors. Micro-focus monochromatized beam typically used with a beam spot size of 250 μm. Sample charge neutralization performed with dual low energy electron flood gun and ion flood source. Energy scale calibrated with a three point calibration curve (Au $4f^{7/2}$, Ag $3d^{5/2}$, Cu $2p^{3/2}$).

Chromium peak data collection: Cr 2p lines and shake up lines from 565 eV to 630 eV.

Typically at least 20 scans collected with a 50 eV pass energy, 0.1 eV step, 50 ms/step.

The following procedure for peak decomposition is used to obtain information regarding chromium forms 1 and 2 (peak positions and relative peak intensities). To clarify, the ratio of chromium form 2 to chromium form 1 is based on the ratio of peak intensities of peak 2 and peak 1, not the ratio of peak areas of peak 2 and peak 1.

a) Background for peak integration: Shirley type background or "Smart" background as used in Thermo Avantage software.

b) Chromium lines peak fitting using a mixed Lorentzian/Gaussian function (mix value=30%). For reference if mix value is 0% the function is purely Gaussian, if mix value is 100% the function is purely Lorentzian).

c) Doublet line separation (Cr $2p^{3/2}$-Cr $2p^{1/2}$) constrained at 9.4 eV±0.5 eV and intensity ratio of the doublet Cr $2p^{1/2}$/Cr $2p^{3/2}$ constrained at 0.512±0.1.

d) Doublet full width at half maximum (FWHM) constrained at 1.0 eV to 3.5 eV for Cr $2p^{3/2}$ and FWHM of Cr $2p^{1/2}$ typically constrained to that of Cr $2p^{3/2}$±0.5 eV, e) Chi-square achieved in refinement typically better than 4.

Example 1

Supported catalyst Ni—Cr/AlF$_3$, four beds (three analyzed).

Catalyst activation: HF, then air treatment.

Reaction conditions: 350° C., 1 bar, HF:1233xf=20-25; molar ratio (O$_2$:1233xf)=0.3–1.8; contact time tc=20-25 s, 2000 hrs total reaction time.

Catalyst bed unloaded at 2000 hrs. When catalyst sample was taken out: Conversion (yf+cb)~40%.

Catalyst bed 1: irreversibly deactivated, even after air treatment.

Catalyst bed 2 to bed 4: expected to still be active.

XPS Results

| Cr2p$^{3/2}$ | 1st bed, brown | 1st bed, green | 2nd bed, brown | 2nd bed, light green | 2nd bed, dark green | 3rd bed, green | 3rd bed, light green |
|---|---|---|---|---|---|---|---|
| Cr2p$^{3/2}$ peak 1 (eV) | 577.4-577.6 | 577.4 | 577.8-578.0 | 577.7 | 577.7 | 577.9 | 577.2-577.6 |
| Cr2p$^{3/2}$ peak 2 (eV) | 580.1-580.2 | 580.2 | 580.5 | 580.6 | 580.9 | 580.9 | 580.5 |

Intensity ratio of the two strongest Cr2p$^{3/2}$ photoelectric peaks for the various catalyst beads of beds 1 to 3.

| Cr2p$^{3/2}$ | 1st bed, brown | 1st bed, green | 2nd bed, brown | 2nd bed, light green | 2nd bed, dark green | 3rd bed, green | 3rd bed, light green |
|---|---|---|---|---|---|---|---|
| peak 2/peak 1 Intensity ratio | 1.55-2.31 | 0.89 | 1.31-1.57 | 2.73 | 4.46 | 3.04 | 2.50-3.17 |
| Bed catalytic status | deactivated | deactivated | Likely active | Likely active | Likely active | Likely active | Likely active |

Example 2

Commercial Bulk catalyst (All experiments described in this example done with the same catalyst specimen—only small fractions unloaded for analysis before re-starting process). Fresh catalyst referenced as "2242C146".

Catalyst activation: HF/N$_2$ (N$_2$/HF=20 by vol); 20 g/h HF, 275° C. Sample "2291C062". Second part of activation is air activation, 50 L/hr down to 10 L/hr, 350° C. Sample "2291C73".

$1^{st}$ run of 1233xf fluorination: tc=20 s, 350° C., HF:1233xf=20 molar ratio, O$_2$:1233xf=4%, 350° C., 1 bar. When catalyst sample was taken out after 95 hrs: Conversion (1233xf)=29.9%, selectivity 1234yf=66.4%, selectivity 245cb=19.1%. Samples "2291C063-067" and "2291C063-067 green".

Air regeneration: 50 L/hr down to 10 L/hr, 350° C., 72 hrs. Sample "2291C68-72".

$2^{nd}$ run of 1233xf fluorination: tc=20 s, 350° C., HF:1233xf=20 molar ratio, $O_2$:1233xf=4%, 350° C. When catalyst sample was taken out after 437 hrs: conversion (1233xf)=63%, selectivity 1234yf=62.1%, selectivity 245cb=28.7%. Sample "2242C185 ter".

Mole concentrations (average concentrations of four specimen for each sample).

|   | 2242C146 Mean ± 2σ | 2291C062 Mean ± 2σ | 2291C73 Mean ± 2σ | 2242C063-067 Mean ± 2σ | 2242C063-067 green Mean ± 2σ | 2291C68-72 Mean ± 2σ | 2242C185 ter Mean ± 2σ |
|---|---|---|---|---|---|---|---|
| C  | 24.2 ± 2.7 | 15.8 ± 2.9 | 21.6 ± 3.2 | 24.1 ± 8.7 | 17.2 ± 3.2 | 22.0 ± 5.4 | 16.9 ± 3.4 |
| Cl | 1.9 ± 0.5 | 0.3 ± 0.1 | 0.3 ± 0.1 | 0.4 ± 0.3 | 0.4 ± 0.1 | 0.2 ± 0.1 | 0.4 ± 0.2 |
| Cr | 23.3 ± 1.1 | 21.8 ± 1.5 | 23.6 ± 1.1 | 17.3 ± 1.0 | 19.3 ± 1.1 | 22.4 ± 1.5 | 18.0 ± 1.4 |
| F  | 1.0 ± 0.5 | 42.7 ± 1.0 | 24.6 ± 1.2 | 48.6 ± 7.1 | 47.7 ± 5.3 | 23.6 ± 18.9 | 52.2 ± 2.4 |
| N  | 0.6 ± 0.2 | 0.7 ± 0.1 | 0.4 ± 0.1 | 0.4 ± 0.2 | 0.5 ± 0.2 | 0.3 ± 0.2 | 0.3 ± 0.1 |
| O  | 47.7 ± 2.3 | 17.8 ± 0.6 | 29.0 ± 1.2 | 8.6 ± 1.0 | 13.4 ± 2.8 | 30.3 ± 11.7 | 11.6 ± 0.6 |
| Zn | 1.4 ± 0.4 | 0.8 ± 0.1 | 0.6 ± 0.1 | 0.7 ± 0.2 | 1.5 ± 0.3 | 1.1 ± 0.5 | 0.7 ± 0.2 |

Chromium Cr $2p^{3/2}$ binding energy and atomic concentration (percents) for chromium forms 1 and 2.

| Binding Energy (eV) | 2242C146 at. conc. (%) | 2291C062 at. conc. (%) | 2291C73 at. conc. (%) | 2242C063-067 at. conc. (%) | 2242C063-067 green at. conc. (%) | 2291C68-72 at. conc. (%) | 2242C185 ter at. conc. (%) |
|---|---|---|---|---|---|---|---|
| 577.3-577.4 "Cr form 1" | 8.0 | 0.4 | 8.7 | 3.7 | 3.5 | 5.2 | — |
| 580.0-580.4 "Cr form 2" | 3.5 |   |   | 8.5 | 13.2 | 9.7 | 14.0 |

Intensity ratio of main chromium Cr $2p^{3/2}$ photoelectric lines.

|   | 2242C146 | 2291C062 | 2291C73 | 2242C063-067 | 2242C063-067 green | 2291C68-72 | 2242C185 ter |
|---|---|---|---|---|---|---|---|
| Peak intensity ratio Cr form 2 (~580 eV)/Cr form 1 (~578 eV) | 0.35 | 1.54 | 0.89 | 2.29 | 3.73 | 1.90 | 8.39 |

Example 3

Commercial Bulk Catalyst.

Catalyst activation: $HF/N_2$ ($N_2$/HF=20 by vol); 20 g/h HF, 275° C. Second part of activation is air activation, 50 L/hr down to 10 L/hr, 350° C.

1233xf fluorination: tc=20 s, 350° C., HF:1233xf=20 molar ratio, $O_2$:1233xf=4%, 350° C., 3 bars, run for 1,888 hrs. When catalyst sample was taken out: conversion (1233xf)=60.5%, selectivity (yf+cb)=95%. Three catalyst samples extracted from bottom, middle, and top of reactor (gas flux goes from top to bottom, so the top catalyst sample is expected to be somewhat less active than the bottom catalyst sample).

Surface Atomic Concentrations (Mole %)

|   | average | 2 * std dev |
|---|---|---|
| OP16 bottom |   |   |
| C  | 11.79 | 1.30 |
| Cl | 0.41 | 0.20 |
| Cr | 19.44 | 0.95 |
| F  | 61.23 | 3.24 |
| O  | 6.36 | 1.30 |
| Zn | 0.77 | 0.10 |
| OP16 middle |   |   |
| C  | 11.13 | 2.86 |
| Cl | 0.70 | 0.09 |
| Cr | 19.24 | 0.78 |
| F  | 61.88 | 1.79 |
| O  | 5.67 | 0.35 |
| Zn | 1.38 | 0.34 |
| OP16 top |   |   |
| C  | 16.32 | 4.24 |
| Cl | 1.30 | 0.31 |
| Cr | 17.76 | 1.48 |

-continued

| | | | |
|---|---|---|---|
| F | | 56.28 | 3.65 |
| O | | 6.96 | 1.46 |
| Zn | | 1.39 | 0.43 |

| Identification | | OP16 bottom Fragment 1 (at. %) | OP16 middle Fragment 2 (at. %) | OP16 top Fragment 1 (at. %) |
|---|---|---|---|---|
| Conversion (%) | | 60.5 | 60.5 | 60.5 |
| Selectivity yf:cb (%) | | 95 | 95 | 95 |
| Cr $2p^{3/2}$, 576.9-578.0 eV | Cr form 1 | 1.83 | 1.20 | 1.58 |
| Cr $2p^{3/2}$, 580.2-580.4 eV | Cr form 2 | 15.22 | 16.36 | 13.92 |
| O 1s, 530.8-531.6 eV | O in Cr form 1 | 0.32 | 0.36 | 1.73 |
| O 1s, 532.4-532.8 eV | O in Cr form 2 | 3.88 | 3.51 | 3.39 |

Chromium and oxygen ratios for form 2 over form 1 for all catalysts. Ratios are obtained from peak heights of the respective chromium and oxygen high-resolution signals.

| | OP16 bottom Fragment 1 | OP16 middle Fragment 2 | OP16 top Fragment 3 |
|---|---|---|---|
| Conversion (%)[1] | 60.5 | 60.5 | 60.5 |
| Selectivity (%) yf:cb[1] | 95 | 95 | 95 |
| $Cr_2/Cr_1$[2] | 8.8 | 11.0 | 7.5 |
| $O_2/O_1$[3] | 14.2 | 7.6 | 2.0 |

Example 4

Commercial Bulk Catalyst.

Catalyst activation: $HF/N_2$ ($N_2/HF=20$ by vol); 20 g/h HF, 275° C. Second part of activation is air activation, 50 L/hr down to 10 L/hr, 350° C.

Fluorination reaction of 1233xf: tc=20 s, 350° C., HF:1233xf=20 molar ratio, $O_2$:1233xf=4%, 350° C., 3 bars, run for 250 hrs. When catalyst sample was taken out: conversion (1233xf)=30%, selectivity (yf+cb)=90%.

Surface atomic concentrations (mole %).

| | Color | | | | | | | |
|---|---|---|---|---|---|---|---|---|
| | light green | grey | grey | grey | grey | light green | grey | grey |
| | "Inner fragment side (rough)" | | | | | "Outer fragment side (smooth)" | | |
| | Fragment 1 | Fragment 2 | Fragment 3 | Fragment 4 | Fragment 5 | Fragment 1 | Fragment 2 | Fragment 3 |
| C | 21.17 | 18.97 | 19.17 | 19.96 | 21.42 | 22.73 | 25.31 | 29.31 |
| Cl | 0.50 | 0.36 | 0.54 | 0.37 | 0.50 | 0.28 | 0.38 | 0.36 |
| Cr | 21.28 | 22.17 | 21.83 | 22.85 | 20.28 | 22.35 | 20.10 | 19.21 |
| F | 44.34 | 44.60 | 46.52 | 40.36 | 45.27 | 36.63 | 41.85 | 39.82 |
| O | 12.02 | 13.27 | 11.28 | 15.36 | 11.90 | 17.32 | 11.74 | 10.50 |
| Zn | 0.70 | 0.62 | 0.65 | 1.11 | 0.63 | 0.70 | 0.61 | 0.79 |

Chromium and oxygen ratios form 2 to form 1. Ratios are obtained from peak heights of the respective chromium and oxygen high-resolution spectra. Conversion was 30% and selectivity about 90% for yf+cb when the catalyst was removed from the reactor.

| | "Inner fragment side (rough)" | | | | | "Outer fragment side (smooth)" | | |
|---|---|---|---|---|---|---|---|---|
| | Frag. 1 | Frag. 2 | Frag. 3 | Frag. 4 | Frag. 5 | Frag. 1 | Frag. 2 | Frag. 3 |
| $Cr_2/Cr_1$[1] | 6.1 | 4.8 | 6.2 | 2.4 | 5.9 | 2.0 | 5.4 | 3.8 |
| $O_2/O_1$[2] | 0.44 | 1.2 | 1.6 | 0.53 | 1.7 | 0.42 | 0.40 | 0.53 |

[1]$Cr_2$ corresponds to chromium form 2 (peak observed around 580.2-581.0 eV). $Cr_1$ corresponds to chromium form 1 (peak observed around 576.9-578.0 eV).

[2]$O_2$ corresponds to oxygen form 2 (peak observed around 532.4-532.8 eV). $O_1$ corresponds to oxygen form 1 (peak observed around 530.8-531.6 eV).

Example 5

Commercial Bulk Catalyst.
Catalyst activation: $HF/N_2$ ($N_2/HF=20$ by vol); 20 g/h HF, 275° C. No air activation was used.
Fluorination reaction of 1233xf: tc=20 s, 350° C., HF:1233xf=20 molar ratio, $O_2$:1233xf=5%, 350° C., 1 bar.
Catalyst sample specimen taken at 24 hrs (conversion 1233xf=32.87%, selectivity yf+cb=75-80%), process re-started under same conditions, then two additional samples taken after an additional 72 hrs (i.e., 96 hrs total on stream) conversion (1233xf)=19.70%, selectivity (yf+cb)=75-80%.
Atomic concentrations (mole %) on surface of catalyst at various stages of F1233xf fluorination (1 atm). Catalyst activated under $HF/N_2$ (no air).

| Side[1] | Inner specimen 1 | Inner specimen 2 | Inner specimen 3 | Inner specimen 4 | Outer specimen 5 | average | 2 * std dev |
|---|---|---|---|---|---|---|---|
| 24 hrs, reactor inlet (conversion = 32.87%; yf:cb selectivity = 75-80%) | | | | | | | |
| C | 20.87 | 19.76 | 18.82 | 27.23 | 34.24 | 24.18 | 13.03 |
| Cl | 0.47 | 0.58 | 0.53 | 0.49 | 0.47 | 0.51 | 0.09 |
| Cr | 22.23 | 22.26 | 22.79 | 20.28 | 19.48 | 21.41 | 2.88 |
| F | 29.66 | 28.96 | 29.32 | 25.92 | 21.48 | 27.07 | 6.92 |
| N | 0.46 | 0.52 | 0.39 | 0.36 | 0.31 | 0.41 | 0.17 |
| O | 25.67 | 27.19 | 26.97 | 25.09 | 23.5 | 25.68 | 3.01 |
| Zn | 0.64 | 0.73 | 1.18 | 0.63 | 0.52 | 0.74 | 0.51 |
| 24 hrs + 72 hrs, reactor inlet (conversion = 19.70%; yf:cb selectivity = 75-80%) | | | | | | | |
| C | 21.81 | 22.71 | 21.39 | 22.90 | 36.79 | 25.12 | 13.11 |
| Cl | 0.65 | 0.46 | 0.59 | 0.40 | 0.40 | 0.50 | 0.23 |
| Cr | 19.75 | 19.44 | 19.83 | 19.32 | 16.85 | 19.04 | 2.48 |
| F | 36.04 | 37.69 | 36.48 | 36.46 | 27.47 | 34.83 | 8.32 |
| N | 0.46 | 0.48 | 0.39 | 0.51 | 0.44 | 0.46 | 0.09 |
| O | 20.76 | 18.70 | 20.67 | 19.90 | 17.58 | 19.52 | 2.73 |
| Zn | 0.53 | 0.51 | 0.65 | 0.51 | 0.47 | 0.53 | 0.14 |
| 24 hrs + 72 hrs, reactor outlet (conversion = 19.70%; yf:cb selectivity = 75-80%) | | | | | | | |
| C | 24.61 | 23.56 | 31.43 | 23.18 | 29.59 | 26.47 | 7.56 |
| Cl | 0.40 | 0.40 | 0.39 | 0.41 | 0.46 | 0.41 | 0.06 |
| Cr | 18.76 | 19.56 | 17.45 | 19.07 | 18.66 | 18.70 | 1.56 |
| F | 35.86 | 35.36 | 31.17 | 36.80 | 30.05 | 33.85 | 6.05 |
| N | 0.46 | 0.38 | 0.53 | 0.53 | 0.46 | 0.47 | 0.12 |
| O | 19.37 | 20.01 | 18.30 | 19.41 | 20.29 | 19.48 | 1.53 |
| Zn | 0.55 | 0.74 | 0.72 | 0.59 | 0.49 | 0.62 | 0.22 |

[1]Inner and outer sides are in reference to the original catalyst pellet, before being fragmented. The inner side of the fragment appears rougher than the outer (shiny) side of the fragment (outer side corresponding to original outside wall of the catalyst cylindrical pellet).

Chemical species identified for fragments 1 of the three samples.

| | Identification | 24 hrs reactor inlet (at. %) | 24 hrs + 72 hrs reactor inlet (at. %) | 24 hrs + 72 hrs reactor outlet (at. %) |
|---|---|---|---|---|
| Conversion (%) | | 32.87 | 19.70 | 19.70 |
| Selectivity yf:cb (%) | | 75-80 | 75-80 | 75-80 |
| Cr $2p^{3/2}$, ~577.2-578.0 eV | Cr form 1 | 6.79 | 5.29 | 4.80 |
| Cr $2p^{3/2}$, 580.2-580.4 eV | Cr form 2 | 7.34 | 7.69 | 7.43 |
| O 1s, 530.8-531.0 eV | O in Cr form 1 | 17.61 | 11.53 | 10.94 |
| O 1s, 532.5-532.8 eV | O in Cr form 2 | 3.97 | 4.99 | 4.28 |

Chromium and oxygen ratios for form 2 over form 1 for all catalysts. Ratios are obtained from peak heights of the respective chromium and oxygen high-resolution signals.

| | 24 hrs reactor inlet | 24 hrs + 72 hrs reactor inlet | 24 hrs + 72 hrs reactor outlet |
|---|---|---|---|
| Conversion (%)[1] | 32.87 | 19.70 | 19.70 |
| Selectivity (%) yf:cb[1] | 75-80 | 75-80 | 75-80 |
| Fragment # | 1 | 1 | 1 |
| $Cr_2/Cr_1$[2] | 0.86 | 1.24 | 1.11 |
| $O_2/O_1$[3] | 0.27 | 0.40 | 0.39 |

[1]Conversion and selectivity at time the catalyst was removed from the reactor.
[2]$Cr_2$ corresponds to chromium form 2 (peak observed around 580.4-581.0 eV). $Cr_1$ corresponds to chromium form 1 (peak observed around 577.0-578.0 eV).
[3]$O_2$ corresponds to oxygen form 2 (peak observed around 532.4-532.8 eV). $O_1$ corresponds to oxygen form 1 (peak observed around 530.3-531.0 eV).

Example 6

Commercial Bulk Catalyst.
Catalyst activation: 5 sccm of $NF_3$ for 24 hrs with catalyst bed at 350° C.

Fluorination of 1233xf: tc=20 s, HF:1233xf:$O_2$=20:1:0.2, 350° C., P=1 bara.

Catalyst sample (conversion 1233xf=<20%, selectivity yf=60%, cb=30%).

TABLE 1.a

Atomic concentrations (mole %) for five fragments of sample 13418-8.

|    | Frag. 1 | Frag. 2 | Frag. 3 | Frag. 4 | Frag. 5 | Average | 2 × std. dev. |
|----|---------|---------|---------|---------|---------|---------|---------------|
| C  | 19.00   | 14.54   | 20.35   | 21.67   | 18.33   | 18.78   | 5.39          |
| Cl | 0.53    | 0.69    | 0.80    | 0.87    | 0.67    | 0.71    | 0.26          |
| Cr | 18.12   | 21.51   | 16.32   | 16.99   | 21.70   | 18.93   | 5.06          |
| F  | 53.28   | 43.39   | 54.07   | 50.35   | 37.52   | 47.72   | 14.18         |
| N  | 0.25    | 0.24    | 0.23    | 0.30    | 0.39    | 0.28    | 0.13          |
| O  | 8.06    | 17.40   | 7.85    | 9.02    | 18.52   | 12.17   | 10.64         |
| Zn | 0.76    | 2.23    | 0.38    | 0.80    | 2.87    | 1.41    | 2.16          |

Chemical species identified for sample 13418-8.

| Identification | | Fragment 1 (at. conc. %) | Fragment 2 (at. conc. %) | Fragment 3 (at. conc. %) | Fragment 4 (at. conc. %) | Fragment 5 (at. conc. %) |
|---|---|---|---|---|---|---|
| Cr $2p^{3/2}$, ~577.2 eV | Cr form 1 | 3.3 | 8.4 | 1.6 | 2.7 | 9.6 |
| Cr $2p^{3/2}$, 580.4-581.0 eV | Cr form 2 | 10.7 | 7.0 | 11.2 | 9.4 | 5.4 |

Chromium and oxygen ratios for form 2 over form 1 for all catalysts. Ratios are obtained from peak heights of the respective chromium and oxygen high-resolution signals.

|  | Sample 13418- | | | | |
|---|---|---|---|---|---|
|  | 8 | 8 | 8 | 8 | 8 |
| Conversion (%)[1] | <20 | <20 | <20 | <20 | <20 |
| Selectivity (%) yf/cb[1] | 60/30 | 60/30 | 60/30 | 60/30 | 60/30 |
| Fragment # | 1 | 2 | 3 | 4 | 5 |
| $Cr_2/Cr_1$[2] | 3.35 | 0.98 | 7.39 | 3.55 | 0.71 |
| $O_2/O_1$[3] | 0.93 | 0.37 | 1.97 | 1.08 | 0.24 |

[1]Conversion and selectivities at time the catalyst was removed from the reactor.
[2]$Cr_2$ corresponds to chromium form 2 (peak observed around 580.4-581.0 eV). $Cr_1$ corresponds to chromium form 1 (peak observed around 577.0-578.0 eV).
[3]$O_2$ corresponds to oxygen form 2 (peak observed around 532.4 eV). $O_1$ corresponds to oxygen form 1 (peak observed around 530.3-530.8 eV).

Example 7

Commercial Bulk Catalyst.

Catalyst activation: 275° C., 5 sccm $NF_3$+100 sccm $N_2$, 24 hrs. Then T=350° C., 5 sccm $NF_3$ only until 642 mmol $NF_3$ added. Then 25 sccm air 4 days, 350° C., P=1 bara.

Fluorination of 1233xf: tc=20 s, HF: 1233xf:$O_2$=20:1: 0.04, 350° C., P=1 bara, 90 hrs.

Re-activation: 10 days, air, T=350° C.

Fluorination of 1233xf: tc=20 s, HF: 1233xf:$O_2$=20:1: 0.04, 350° C., P=1 bara, 260 hrs.

Re-activation: 3 days, air, T=350° C.

Fluorination of 1233xf: tc=20 s, HF: 1233xf:$O_2$=20:1: 0.04, 350° C., P=1 bara, 400 hrs.

Catalyst sample (final conversion 1233xf=35%, final selectivity yf=35-40%, selectivity cb=57-62%).

Atomic concentrations (mole %) for five fragments of sample 13418-53.

|    | Frag. 1 | Frag. 2 | Frag. 3 | Frag. 4 | Frag. 5 | Average | 2 × std. dev. |
|----|---------|---------|---------|---------|---------|---------|---------------|
| C  | 15.04   | 16.12   | 15.33   | 15.15   | 15.12   | 15.35   | 0.88          |
| Cl | 0.62    | 0.57    | 0.64    | 0.64    | 0.64    | 0.62    | 0.06          |
| Cr | 17.74   | 17.51   | 18.08   | 17.55   | 18.00   | 17.78   | 0.52          |
| F  | 60.97   | 59.55   | 59.97   | 60.81   | 56.29   | 59.52   | 3.80          |
| N  | 0.26    | 0.37    | 0.19    | 0.37    | 0.77    | 0.39    | 0.45          |
| O  | 4.81    | 5.33    | 5.20    | 4.91    | 8.68    | 5.79    | 3.26          |
| Zn | 0.56    | 0.55    | 0.59    | 0.57    | 0.50    | 0.55    | 0.07          |

Chemical species identified for sample 13418-53.

|  | Identification | 13418-53 Fragment 2 (at. conc. %) |
|---|---|---|
| Cr $2p^{3/2}$, ~577.1 eV | Cr form 1 | 1.2 |
| Cr $2p^{3/2}$, 580.4-581.0 eV | Cr form 2 | 11.4 |

Chromium and oxygen ratios for form 2 over form 1 for all catalysts. Ratios are obtained from peak heights of the respective chromium and oxygen high-resolution signals.

|  | Sample 13418-53 |
|---|---|
| Conversion (%)[1] | ~40 |
| Selectivity (%) yf/cb[1] | 40/57 |
| Fragment # | 2 |
| $Cr_2/Cr_1$[2] | 8.88 |
| $O_2/O_1$[3] | 30.0 |

[1]Conversion and selectivities at time the catalyst was removed from the reactor.
[2]$Cr_2$ corresponds to chromium form 2 (peak observed around 580.4-581.0 eV). $Cr_1$ corresponds to chromium form 1 (peak observed around 577.0-578.0 eV).
[3]$O_2$ corresponds to oxygen form 2 (peak observed around 532.4 eV). $O_1$ corresponds to oxygen form 1 (peak observed around 530.3-530.8 eV).

Example 8

Commercial Bulk Catalyst.

Catalyst activation: 5 sccm of $NF_3$ for 24 hrs with catalyst bed at 350° C.

Fluorination of 1233xf: tc=20 s, HF:1233xf:$O_2$=20:1:0.2, 350° C., P=1 bara, 300 hrs.

Re-activation: $NF_3$ 18 hrs, 350° C., 5 sccm $NF_3$.

Fluorination of 1233xf: tc=20 s, HF: 1233xf:$O_2$=20:1:0.2, 350° C., P=1 bara, 550 hrs.

Catalyst sample (conversion 1233xf=40%, selectivity yf=68%, cb=35%).

Atomic concentrations (mole %) for five fragments of sample 13418-94.

|     | Frag. 1 | Frag. 2 | Frag. 3 | Frag. 4 | Frag. 5 | Average | 2 × std. dev. |
|-----|---------|---------|---------|---------|---------|---------|---------------|
| C   | 14.71   | 14.49   | 13.55   | 14.10   | 10.83   | 13.54   | 3.15          |
| Cl  | 0.23    | 0.32    | 0.54    | 0.20    | 0.15    | 0.29    | 0.31          |
| Cr  | 17.53   | 17.11   | 19.08   | 17.94   | 19.36   | 18.20   | 1.96          |
| F   | 62.66   | 62.70   | 59.91   | 62.29   | 65.02   | 62.52   | 3.63          |
| N   | 0.48    | 0.70    | 0.23    | 0.40    | 0.39    | 0.44    | 0.34          |
| O   | 3.83    | 4.19    | 6.00    | 4.63    | 3.83    | 4.50    | 1.81          |
| Zn  | 0.56    | 0.49    | 0.69    | 0.44    | 0.42    | 0.52    | 0.22          |

Chemical species identified for sample 13418-94.

|                                | Identification | 13418-94 Fragment 3 (at. conc. %) |
|--------------------------------|----------------|-----------------------------------|
| Cr $2p^{3/2}$, ~577.1 eV       | Cr form 1      | 1.8                               |
| Cr $2p^{3/2}$, 580.4-581.0 eV  | Cr form 2      | 13.1                              |

Chromium and oxygen ratios for form 2 over form 1 for all catalysts. Ratios are obtained from peak heights of the respective chromium and oxygen high-resolution signals.

|                      | Sample 13418-94 |
|----------------------|-----------------|
| Conversion (%)[1]    | ~40             |
| Selectivity (%) yf/cb[1] | 68/35       |
| Fragment #           | 3               |
| $Cr_2/Cr_1$[2]       | 6.63            |
| $O_2/O_1$[3]         | 22.0            |

[1]Conversion and selectivities at time the catalyst was removed from the reactor.
[2]$Cr_2$ corresponds to chromium form 2 (peak observed around 580.4-581.0 eV). $Cr_1$ corresponds to chromium form 1 (peak observed around 577.0-578.0 eV).
[3]$O_2$ corresponds to oxygen form 2 (peak observed around 532.4 eV). $O_1$ corresponds to oxygen form 1 (peak observed around 530.3-530.8 eV).

What is claimed is:

1. A chromium oxyfluoride catalyst active for fluorination of a chlorinated compound, wherein the chromium oxyfluoride catalyst is comprised of a first chromium species and a second chromium species, wherein the first chromium species exhibits a first X-ray photoelectron spectroscopy (XPS) chromium Cr $2p^{3/2}$ peak between 576.9 eV+/−0.2 eV and 578.0 eV+/−0.2 eV and the second chromium species exhibits a second X-ray photoelectron spectroscopy (XPS) chromium Cr $2p^{3/2}$ peak between 580.0 eV+/−0.2 eV and 581.4 eV+/−0.2 eV and wherein the intensity of the second XPS chromium peak is greater than the intensity of the first XPS chromium peak.

2. The chromium oxyfluoride catalyst of claim 1, wherein the chromium oxyfluoride catalyst is a supported catalyst.

3. The chromium oxyfluoride catalyst of claim 1, wherein the chromium oxyfluoride catalyst is a catalyst supported on an aluminum-containing support.

4. The chromium oxyfluoride catalyst of claim 2, wherein the ratio of the intensity of the second XPS chromium peak to the intensity of the first XPS chromium peak is greater than 2.5.

5. The chromium oxyfluoride catalyst of claim 1, wherein the chromium oxyfluoride catalyst is a bulk catalyst.

6. The chromium oxyfluoride catalyst of claim 5, wherein the ratio of the intensity of the second XPS chromium peak to the intensity of the first XPS chromium peak is greater than 8.0.

7. The chromium oxyfluoride catalyst of claim 1, wherein the chromium oxyfluoride catalyst is comprised of a first oxygen species and a second oxygen species, wherein the first oxygen species exhibits a first X-ray photoelectron spectroscopy (XPS) oxygen O 1 s peak between 530.3 eV±0.2 eV and 531.6 eV±0.2 eV and the second oxygen species exhibits a second X-ray photoelectron spectroscopy (XPS) oxygen O 1 s peak between 532.4 eV±0.2 eV and 532.8 eV±0.2 eV and wherein the intensity of the second XPS oxygen peak is greater than the intensity of the first XPS oxygen peak.

8. The chromium oxyfluoride catalyst of claim 7, wherein the ratio of the intensity of the second XPS oxygen O 1 s peak to the intensity of the first XPS oxygen O 1 s peak is greater than 2.

9. The chromium oxyfluoride catalyst of claim 1, wherein the energy shift between the first XPS chromium Cr $2p^{3/2}$ peak and the second XPS chromium Cr $2p^{3/2}$ peak is 3.3 eV±1.7 eV.

10. The chromium oxyfluoride catalyst of claim 1, wherein the chromium oxyfluoride catalyst is modified with at least one metal selected from the group consisting of Zn, Co, Ni, Mn, Mg and combinations thereof.

11. A method of assessing the activity of a chromium oxyfluoride catalyst for fluorination of a chlorinated compound, wherein the method comprises analyzing the chromium oxyfluoride catalyst by X-ray photoelectron spectroscopy (XPS) to measure the relative intensities of a first XPS chromium Cr $2p^{3/2}$ peak between 576.9 eV+/−0.2 eV and 578.0 eV+/−0.2 eV associated with a first chromium species and a second XPS chromium Cr $2p^{3/2}$ peak between 580.0 eV+/−0.2 eV and 581.4 eV+/−0.2 eV associated with a second chromium species.

12. A method of fluorinating a chlorinated compound, comprising contacting the chlorinated compound and hydrogen fluoride in gas phase in the presence of a chromium oxyfluoride catalyst in accordance with claim 1 to produce a fluorinated compound.

13. The method of claim 12, wherein the chlorinated compound is 1,1,2,3-tetrachloropropene and the fluorinated compound is HFO-1234yf or the chlorinated compound is 2-chloro-3,3,3-trifluoropropene and the fluorinated compound is HFO-1233xf.

14. A method of making a chromium oxyfluoride catalyst active for fluorination of a chlorinated compound, wherein the method comprises preparing the chromium oxyfluoride catalyst under conditions effective to provide a chromium oxyfluoride catalyst wherein the intensity of a first XPS chromium Cr $2p^{3/2}$ peak between 576.9 eV+/−0.2 eV and 578.0 eV+/−0.2 eV associated with a first chromium species in the chromium oxyfluoride catalyst is less than the intensity of a second XPS chromium Cr $2p^{3/2}$ peak between 580.0 eV+/−0.2 eV and 581.4 eV+/−0.2 eV associated with a second chromium species.

15. A method of making a chromium oxyfluoride catalyst active for fluorination of a chlorinated compound, comprising the following stages, in succession: a) an unactivated catalyst preparation stage, wherein an unactivated chromium oxyfluoride catalyst is prepared; b) a first activation stage, wherein the unactivated catalyst is subjected to activation conditions to obtain a first activated chromium oxyfluoride catalyst; c) a catalyst evaluation stage, wherein the first activated chromium oxyfluoride catalyst is analyzed by XPS to measure the relative intensities of a first XPS chromium Cr $2p^{3/2}$ peak between 576.9 eV+/−0.2 eV and 578.0 eV+/−0.2 eV and a second XPS chromium Cr $2p^{3/2}$ peak between 580.0 eV+/−0.2 eV and 581.4 eV+/−0.2 eV; and either d1) a second activation stage, wherein the first activated chromium oxyfluoride catalyst is further subjected to activation conditions to obtain a second activated chromium oxyfluoride catalyst, if the intensity of the first XPS chromium Cr $2p^{3/2}$ peak is not less than the intensity of the second XPS chromium Cr $2p^{3/2}$ peak or d2) a reaction stage wherein a chlorinated compound is contacted with hydrogen fluoride in gas phase in the presence of the first activated chromium oxyfluoride catalyst to produce a fluorinated compound, if the intensity of the first XPS chromium Cr $2p^{3/2}$ peak is less than the intensity of the second XPS chromium Cr $2p^{3/2}$ peak.

16. A method of regenerating a spent chromium oxyfluoride catalyst improve its activity for fluorination of a chlorinated compound, wherein the method comprises regenerating the chromium oxyfluoride catalyst under conditions effective to provide a chromium oxyfluoride catalyst wherein the intensity of a first XPS chromium Cr $2p^{3/2}$ peak between 576.9 eV+/−0.2 eV and 578.0 eV+/−0.2 eV associated with a first chromium species present in the chromium oxyfluoride catalyst is less than the intensity of a second XPS chromium Cr $2p^{3/2}$ peak between 580.0 eV+/−0.2 eV and 581.4 eV+/−0.2 eV associated with a second chromium species.

17. A method, comprising the following steps in succession: a) a first reaction stage wherein a chlorinated compound is contacted with hydrogen fluoride in gas phase in the presence of a chromium oxyfluoride catalyst to produce a fluorinated compound, wherein the first reaction stage is carried out for a length of time sufficient to cause the activity of the chromium oxyfluoride catalyst to fall below a selected value; b) a first reactivation stage, wherein the chromium oxyfluoride catalyst is subjected to reactivation conditions to obtain a first reactivated chromium oxyfluoride catalyst; c) a catalyst evaluation stage, wherein the first reactivated chromium oxyfluoride catalyst is analyzed by XPS to measure the relative intensities of a first XPS chromium Cr $2p^{3/2}$ peak between 576.9 eV+/−0.2 eV and 578.0 eV+/−0.2 eV and a second XPS chromium Cr $2p^{3/2}$ peak between 580.0 eV+/−0.2 eV and 581.4 eV+/−0.2 eV; and either d1) a second reactivation stage, wherein the chromium oxyfluoride catalyst is further subjected to reactivation conditions to obtain a second reactivated chromium oxyfluoride catalyst, if the intensity of the first XPS chromium Cr $2p^{3/2}$ peak is not less than the intensity of the second XPS chromium Cr $2p^{3/2}$ peak or d2) a second reaction stage wherein a chlorinated compound is contacted with hydrogen fluoride in gas phase in the presence of the first reactivated chromium oxyfluoride catalyst to produce a fluorinated compound, if the intensity of the first XPS chromium Cr $2p^{3/2}$ peak is less than the intensity of the second XPS chromium Cr $2p^{3/2}$ peak.

* * * * *